(12) United States Patent
Kropf et al.

(10) Patent No.: US 6,858,214 B1
(45) Date of Patent: Feb. 22, 2005

(54) USE OF NANOSCALAR WATER-SOLUBLE β-(1,3) GLUCANS

(75) Inventors: Christian Kropf, Dusseldorf (DE); Ute Griesbach, Dusseldorf (DE); Bernd Fabry, Korschenbroich (DE); Rolf E. Engstad, Tromso (NO)

(73) Assignee: Biotec ASA, Tromso (NO)

( * ) Notice: Subject to any disclaimer, the term of this patent is extended or adjusted under 35 U.S.C. 154(b) by 0 days.

(21) Appl. No.: 09/936,747

(22) PCT Filed: Mar. 3, 2000

(86) PCT No.: PCT/EP00/01829

§ 371 (c)(1),
(2), (4) Date: Feb. 15, 2002

(87) PCT Pub. No.: WO00/54741

PCT Pub. Date: Sep. 21, 2000

(30) Foreign Application Priority Data

Mar. 12, 1999 (DE) .......................................... 199 11 058

(51) Int. Cl.$^7$ ...................... A61K 7/00; A61K 31/175; A61K 35/78
(52) U.S. Cl. .................. 424/401; 424/195.16; 424/400; 514/54
(58) Field of Search .......................... 424/59, 400, 401, 424/195.16; 514/54

(56) References Cited

U.S. PATENT DOCUMENTS

| 4,333,927 A | * | 6/1982 | Ofuchi et al. ................ 514/174 |
| 5,376,173 A | * | 12/1994 | Haze et al. .................. 106/804 |
| 5,688,775 A | * | 11/1997 | Renn et al. .................... 514/54 |
| 5,705,184 A | | 1/1998 | Donzis |
| 6,143,883 A | * | 11/2000 | Lehmann et al. .......... 536/55.3 |

FOREIGN PATENT DOCUMENTS

| JP | 55027126 | 2/1980 |
| WO | WO9530022 | 11/1995 |
| WO | WO 96/28476 A1 * | 9/1996 |
| WO | WO9911695 | 3/1999 |

* cited by examiner

*Primary Examiner*—Gary Kunz
*Assistant Examiner*—Marina Lamm
(74) *Attorney, Agent, or Firm*—Ladas & Parry LLP

(57) ABSTRACT

The invention relates to the use of nanoscalar water-soluble β-(1,3) glucans, which are essentially free from β-(1,6) links and have particle diameters ranging from 10 to 300 nm for producing cosmetic and/or pharmaceutical preparations. When applied topically, the especially fine dispersion of the particles, compared to prior art glucans, facilitates their rapid penetration of both the stratum corneum of the skin and the keratin fibres of the hair.

14 Claims, No Drawings

US 6,858,214 B1

USE OF NANOSCALAR WATER-SOLUBLE β-(1,3) GLUCANS

THE FIELD OF INVENTION

The invention belongs to the field of the nano particles and concerns the use of specific nanoscalar β-(1,3) glucans in cosmetics.

PRIOR ART

Homopolysaccharides based on glucose are known under the term glucans. Depending on sterical linkage difference is made between β-(1,3), β-(1,4) and β-(1,6) glucans. β-(1,3) Glucans are generally showing a helical structure, while glucans with a 1,4-linkage usually have a linear structure. Glucans and their derivatives have on various occasions been proposed for use in cosmetics. From the patent U.S. Pat. No. 5,223,491 is a carboxymethylated β-1,3 glucan for topical application known, which has been extracted from the yeast fungus *Saccharomyces cerevisiae*. The glucan is, however, insoluble in water and is accordingly very difficult to formulate. Known from the European patent EP-B1 0500718 (Donzis) is the use of β-(1,3) glucans which are insoluble in water, and which are obtained from the cell walls of yeast, for revitalization of the skin. These glucans are, however, insoluble in water and are therefore only with difficulties blendable in cosmetic preparations. The object of the international patent application WO 98/40082 (Henkel) is indeed the use of water soluble β-(1,3) glucans as active agents for treatment of the skin. The glucans, which preferably are schizopyhallan or krestin, i.e extracts of fungus, have been shown to be inadequately effective in practice.

The effect of the glucans is always connected with the rate with which the compounds are built-in, respectively resorbed. In this connection the available materials of prior art still have a substantial potential for improvement. The task of the instant invention was therefore to accelerate the absorption of glucans by topical application by making available novel administration forms.

DESCRIPTION OF THE INVENTION

The object of the invention is the use of nanoscalar water soluble β-(1,3) glucans, which are substantially free from (1,6)-linkages and with particle diameters in the range of 10 to 300 nm, for the production of cosmetic and/or pharmaceutical preparations.

Surprisingly, it was found that the resorption of water soluble β-(1,3) glucans, which are substantially free from (1,6) linkages, both through the stratum corneum of the skin as also the keratin fibrils of the hair can be significantly increased, when these are present in the form of nano particles, i.e. particels with an average diameter in the range from 10 to 300 and preferably 50 to 150 nm.

Water Soluble β-(1,3) Glucans

The β-glucans of the invention have a (1,3) structure, i.e. they are substantillay free from undesired (1,6) linkages. Especially the agents contain glucans which are obtained on the basis of yeast from the family *Sacchaomyces*, especially *Saccharomyces cerevisiae*. Glucans of this type are available in technical amounts according to known methods. The international patent application WO 95/30022 (Biotec-Mackzymal) describes a method for producing such substances, wherein glucans with β-(1,3) and β-(1,6) linkages are brought in contact with β-(1,6) glucanases in such a way, that practically all β-(1,6) linkages are loosened. Preferably such β-(1,3) glucans are used whose side chains only have (1,3) linkages. For the manufacture of the glucans are glucanases based on *Trichodermia harianum* preferably used. As to the manufacture and availability of the glucans contained in these agents, reference is made to the above cited publication.

Production of Nanoparticles

A metod for prodction of nano particles by rapig relaxation of supercritical solutions (Rapid Expansion of Supercritical Solutions RESS) is for example known from the paper of S.Chihlar, M.Turk and K.Schaber in *Proceedings World Congress on Pardcle Technology* 3, Brighton, 1998. A method for the manufacturing of the nano particles consists of (a) dissolving the water soluble β-(1,3) glucans under superkritical or close to critical conditions in a suitable solvent,
(b) relaxing of the fluid mixture through a nozzle in a vacuum, a gas or a liquid, and
(c) at the same time evaporation of the solvent.

To prevent that the nano particles again agglomerate, it is recommended to dissolve the starting materials in the presence of suitable protective colloids or emulsifiers and/or to relax the critical solutions in aqueous and/or alcoholic solutions of the protection colloids or emulsifiers or, to relax into cosmetic oils, which also can contain dissolved emulsifiers and/or protection colloids. Suitable protection colloids are in this case e.g. gelatine, casein, gum arabicum, lysabic acid, starch, as well as polymers, such as polyvinyl alcohols, polyvinyl pyrrolidone, polyakylene glycol and polyacrylate. The nanoscale glucans which are preferably used, are thereby the glucans which are surrounded by a protection colloid and/or an emulsifier. Normally the protection colloids or emulsifiers are used in amounts from 0,1 to 20, preferably 5 to 15% by weight, based on the glucans.

An additional suitable method for production of the nanoscale particles is offered by the evaporation technique. In this case the starting materials initially are dissolved in a suitable organic solvent (e.g. alkanes, vegetable oils, ethers, esters, ketones, acetals, etc.). Thereafter the solutions are added to water or another non-solvent, possibly in the presence of a surfactant dissolved therein, so that the homogenisation of both non-miscible solvents will result in a precipitation of the nano particles, whereby the organic solvent preferably evaporates. Instead of an aqueous solution also O/W-emulsions, respectively O/W-micro emulsions, can be used. As surface active agents the already above mentioned emulsifiers and protection colloids can be used. A further possiblity for the production of nano particles is the use of the so called GAS method (Gas Anti Solvent Recrystallization). The method uses a highly compressed gas or supercritical fluid (e.g. carbon dioxide) as non-solvent for the crystallization of dissolved materials. The compressed gas phase is introduced into the primary solution of the starting materials where it is absorbed, whereby the volume of the liquid is increased, the solubility decreased and fine particles are precipitated. Also suitable is the PCA method (Precipitation with a Compressed Fluid Anti-Solvent). Here the primary solution of the initial materials is introduced into a supercritical fluid, whereby finely distributed small drops are being formed, in which diffusion procedures take place, so that a precipitation of very fine particles occurs. In the PGSS method (Particles from Gas Saturated Solutions) the initial substances are melted by pressing thereon of a gas (e.g. carbon dioxide or propane).

Pressure and temperature reach close to critical or supercritical conditions. The gas phase dissolves in the solids and leads to a reduction of the melting temperature, the viscosity and the surface tension. By the expansion through a nozzle the cooling effects lead to the formation of fine particles.

Commercial Applicability

In relation to glucans, especially water soluble β-(1,3) glucans, which likewise are substantially free from unwanted (1,6) linkages, and thereby is the closest prior art, the particular fineness of the particles by topical use leads to their faster penetration into the stratum corneum. The required quantity of the nanoscalar compounds normally lies in the order of magnitude from 0,1 to 5, preferably 0,5 to 3 and especially 1 to 2% by weight, based on the preparations.

Cosmetical and/or Pharmaceutical Preparations

The preparations which can be obtained by use according to the inventien, of the nanoscalar β-(1,3) glucans, such as e.g. hair shampoos, hair lotions, foam baths, shower baths, cremes, gels, lotions, alcohol and/or water solutions, emulsions, masses of wax/fat, stick preparations, powders or ointments, can further as additional auxiliary or additional substances contain mild surfactants, oil bodies, emulsifiers, hyperfatting agents, pearl lustre waxes, consistency substances, thickening agents, polymers, silicon compounds, fats, waxes, stabilizing agents, biogenic active substances, deodorants, agents against dandruff, film forming agents, swelling agents, UV light protection factors, antioxidants, inorganic colour pigments, hydrotropes, preservatives, insect repellents, self tanning agents, solubilizing agents, perfume oils, colouring agents, germ inhibiting agents and suchlike.

Typical examples of suitable mild, i.e. especially skin compatible surfactants, are fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, α-olefine sulphonates, ethercarboxylic acids, alkyl oligoglucosides, fatty acid glucamides, alkylamido betaines and/or protein fatty acid condensates, the last mentioned preferably based on wheat proteins.

As oil bodies use can be made of for example Guerbet alcohols based on fatty alcohols with 6 to 18, preferably 8 to 10 carbon atoms, esters of linear $C_6$–$C_{22}$ fatty acids with linear $C_6$–$C_{22}$ fatty alcohols, esters of branched $C_6$–$C_{13}$ carboxylic acids with linear $C_6$–$C_{22}$ fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isosteayl behenate, isostearyl oleate, oleyl myristate, oleyl palmitate, oleyl stearate, oleyl isostearate, oleyl oleate, oleyl behenate, oleyl enucate, behenyl myristate, behenyl palmitate, behenyl stearate, behenyl isostearate, behenyl oleate, behenyl behenate, behenyl erucate, erucyl myristate, erucyl palmitate, enucyl stearate, erucyl isostearate, erucyl oleate, erucyl behenate and erucyl erucate. In additon esters of linear $C_6$–$C_{22}$ fatty acids with branched alcohols, especially 2-ethylhexanol, esters of hydroxycarboxylic acids with linear or branched $C_6$–$C_{22}$ fatty alcohols, especially dioctyl malate, esters of linear and/or branched fatty acids with polyvalent alcohols (such as e.g. propylene glycol, dimeric diol or trimeric triol) and/or Guerbet alcohols, triglycerides based on $C_6$–$C_{10}$ fatty acids, liquid mixtures of mono-/di-/triglycerides based on $C_6$–$C_{18}$ fatty acids, esters of $C_6$–$C_{22}$ fatty alcohols and/or Guerbet alcohols with aromatic carboxylic acids, especially benzoic acid, esters of $C_2$–$C_{12}$ dicarboxylic acids with linear or branched alcohols with 1 to 22 carbon atoms or polyols with 2 to 10 carbon atoms and 2 to 6 hydroxyl groups, plant oils, branched primary alcohols, substituted cyclohexanes, linear and branched $C_6$–$C_{22}$ fatty alcohol carbonates, Guerbet carbonates, esters of benzoic acid with linear and/or branched $C_6$–$C_{22}$ alcohols (e.g. Finsolva ® TN), linear or branched, symmetrical or unsymmetrical dialkyl ethers with 6 to 22 carbon atoms in each alkyl group, ring opening products of epoxydated fatty acid esters with polyols, silicone oils and/or aliphatic or naphthenic hydrocarbons, such as e.g. squalan, squalen or dialkyl cyclohexanes, can be used As emulsifiers for example nonionic surfactants from at least one of the following groups may be used:

(1) Addition products of 2 to 30 moles ethylene oxide and/or 0 to 5 moles propylene oxide on linear fatty alcohols with 8 to 22 C atoms, on fatty acids with 12 to 22 C atoms and on alkyl phenols with 8 to 15 C atoms in the alkyl group;
(2) $C_{12/18}$ fatty acid mono- and -diesters of addition products of 1 to 30 moles ethylene oxide and glycerol;
(3) glycerol mono- and diesters and sorbitan mono- and diesters of saturated and unsaturated fatty acids with 6 to 22 carbon atoms and their ethylene oxide addition products;
(4) alkyl mono- and oligoglycosides with 8 to 22 carbon atoms in the alkyl group and their ethoxylated analogues;
(5) addition products of 15 to 60 moles ethylene oxide on ricinus oil and/or hardened ricinus oil;
(6) polyol and especially polyglycerol esters, such as e.g. polyglycerol polyricinoleate, polyglycerol poly-12-hydroxystearate or polyglycerol dimerate isostearate, and also mixtures of compounds from more of these classes of substances;
(7) addition products of 2 to 15 moles ethylene oxide on ricinus oil and/or hardened ricinus oil;
(8) partial esters based on linear, branched, unsaturated or saturated $C_{6/22}$ fatty acids, ricinolic acid and 12-hydroxy stearic acid and glycerol, polyglycerol, pentaerythrite, dipentaerythrite, sugar alcohols (e.g. sorbitol), alkyl glucosides (e.g. methyl glucoside, butyl glucoside, lauryl glucoside) as well as polyglucosides (e.g. cellulose);
(9) mono-, di- and trialkylphosphates as well as mono-, di- and/or tri-PEG alkylphosphates and their salts;
(10) wool wax alcohols;
(11) polysiloxane/polyalkyl/polyether copolymers or corresponding derivatives;
(12) mixed esters of pentaerythrite, fatty acids, citric acid and fatty alcohol according to DE 1165574 PS and/or mixed esters of fatty acids with 6 to 22 carbon atoms, methyl glucose and polyols, preferably glycerol or polyglycerol,
(13) polyalkylene glycols, as well as
(14) glycerol carbonate.

The addition products of ethylene oxide and/or of propylene oxide on fatty alcohols, fatty acids, alkyl phenols, glycerol mono- and diesters as well as sorbitan mono- and -diesters of fatty acids or on ricinus oil are known products which are commercially available. They are mixtures of homologous substances, with average degree of alkoxylation corresponding to the ratio of the amounts of the substances ethylene oxide and/or propylen oxide and substrate, with which the addition reaction is carried out. $C_{12/18}$ fatty acid mono- and -diesters of addition products of ethylene oxide on glycerol are known from DE 2024051 PS as revertive fafting agents for cosmetic preparations.

$C_{8/18}$ alkyl mono- and oligoglycosides, their manufacture and their use is known from prior art. Their preparation can especially be carried out by reaction of glucose or oligosaccharides with primary alcohols having 8 to 18 C atoms. With regard to the glycoside residue both monoglycosides, where a cyclic sugar group is glycosidic bond to the fatty alcohol, and oligomeric glycosides with a degree of oligomerisation until preferably about 8, are suitable. The degree of oligomerization is then a statistical mean value, based on a distribution of homologues which is usual for such products of technical quality.

Zwitterionic surfactants can also be used as emulsifiers. The term zwitterionic surfactants is intended to mean such surface active compounds which in their molecule have at least a quatenary ammonium group and at least one carboxylate and one sulphonate group. Especially suitable zwitterionic surfactants are the so-called betaines such as the N-alkyl-N,N-dimethyl ammonium glycinates, for example the coco alkyldimethyl ammonium glycinate, N-acylamino propyl-N,N-dimethyl ammonium glycinate, for example the coco acylaminopropyl dimethyl ammonium glycinate, and 2-alkyl-3-carboxylmethyl-hydroxyethyl imidazoline with in each case 8 to 18 C atoms in the alkyl or acyl groups, as well as the coco acylaminoethyl hydroxyethylcarboxymethyl glycinate. Especially preferred is that under the CTFA term cocamidopropyl betaine known fatty acid amide derivative. Also suitable emulsifiers are ampholytic surfactants. Ampholytic surfactants are such surface active compounds which in addition to a $C_{8/18}$ alkyl or acyl group in the molecule at least contain a free amino group and at least one —COOH or —$SO_3H$ group and which can form inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkylami-dopropyl glycines, N-alkyltaurines, N-alkylsarcosines, 2-alkylaminopropionic acids and alkylamino acetic acids with in each case about 8 to 18 C atoms in the alkyl group. Especially preferable ampholytic surfactants are the N-coco alkylamino propionate, the coco acylamino ethylaminopropionate and the $C_{12/18}$ acyl sarcosine. In addition to the ampholytic, also quatemary emulsifiers can be used, of which ester salts of the type of esterquats, preferably methyiquatemised di-fatty acid triethanolamine ester salts, are especially preferable.

As hyperfatting agents substances such as for example lanolin and lecithin as well as polyethoxylated or acylated lanolin and lecithin derivatives, polyol fatty acid esters, monoglycerides and fatty acid alkanolamides can be used, whereby the last mentioned at the same time act as foam stabilisers.

As exemplary pearl gloss waxes the following should be mentioned: Alkylene glycolester, especially ethyleneglycol distearate; fatty acid alkanolamides, especially coco fatty acid diethanolamide; partial glycerides, especially stearic acid monoglyceride; esters of polyvalent, possibly hydroxysubstituted carboxylic acids with fatty alcohols with 6 to 22 carbon atoms, especially long chain esters of tartaric acid; fat substances, such as for example fatty alcohols, fatty ketones, fatty aldehydes, fatty ethers and fatty carbonates, wherin the sum of carbon atoms is at least 24, especially lauron and distearylether; fatty acids such as stearic acid, hydroxystearic acid or behenic acid, ring opening products of olefine epoxides with 12 to 22 carbon atoms with fatty alcohols with 12 to 22 carbon atoms and/or polyols with 2 to 15 carbon atoms and 2 to 10 hydroxyl groups as well as their mixtures.

As consistency givers preferably use is made of fatty alcohols or hydroxy fatty alcohols with 12 to 22 and preferably 16 to 18 carbon atoms and additionally partial giycerides, fatty acids or hydroxy fatty acids. A combination of these substances with alkyl oligoglucosides and/or fatty acid-N-methyl glucamides with the same chain length and/or polyglycerol-poly-12-hydroxy stearates.

Suitable thickening agents are for example types of aerosil (hydrophilic silicic acids), polysaccharides, especially xanthan gum, guar-guar, agar-agar, alginates and tyloses, carboxymethyl celluloses and hydroxyethyl celluloses, as well as higher molecular polyethylenglycol mono- and diesters of fatty acids, polyacrylates, (e.g. Carbopols® from Goodrich or Synthaleneso from Sigma), poly-acrylamides, polyvinyl alcohol and polyvinyl pyrrolidone, surfactants such as for example ethoxylated fatty acid glycerides, ester of fatty acids with polyols such as for example pentaerythrite or trimethylolpropane, fatty alcohol ethoxytates with narrow distribution of homologous or alkyl oligoglucosides as well as elektrolytes such as sodium chloride and ammonium chloride.

Suitable cationic polymers are for example cationic cellulose derivatives, such as e.g. a quaternized hydroxyethyl cellulose, which is available under the name of Polymer JR 400® from Amerchol, cationic starch, copolymers of diallyl ammonium salts and acrylamides, quatemized vinylpyrrolidine/vinylimidazol polymers, such as e.g. Luviquat® (BASF), condensation products of polyglycols and amines, quaternized collagen polypeptides, such as for example lauryl dimonium hydroxypropyl hydrolyzed collagen (Lamequat®L/Grünau), quaternized wheat polypeptides, polyethyleneimine, cationic silicone polymers, such as e.g. amidomethicones, copolymers of adipic acid and dimethylamino hydroxypropyl diethylenetriamine (Cartaretine®/Sandoz), copolymers of acrylic acid with dimethyl diallylammonium chloride (Merquat®550/Chemviron), polyamino pdlyamides, such as e.g. described in FR 2252840 A, as well as their cross-linked water soluble polymers, cationic chitin derivatives such as for example quatemized chitosan, possibly micro crystalline distributed, condensation products of dihalogen alkyls, such as e.g. dibromobutane with bisdialkylamines, such as e.g. bis-dimethylamino-1,3-propane, cationic guar-gum, such as e.g. Jaguar® CBS, Jaguar® C-17, Jaguar® C-16 from Celanese, quaternised ammonium salt polymers, such as e.g. Mirapol® A-15, Mirapol® AD-1, Mirapol® AZ-1 from Miranol.

As exemplary anionic, zwitterionic, amphoteric and nonionic polymers the following can be used: Vinyl acetate/crotonic acid copolymers, vinyl pyrrolidone/vinyl acrylate copolymers, vinyl acetate/butyl maleate/isobornyl acrylate copolymers, methyl vinylether/maleic acid anhydride copolymers and their esters, non-cross-linked and with polyols cross-linked polyacrylic acids, acrylamido propyltrimethyl ammonium chloride/acrylate copolymers, octylacryl amide/methyl methacrylate/tert.-butylaminoethyl methacrylate/2-hydroxypropyl-methacrylate copolymers, polyvinylpyrrolidone, vinylpyrrolidone/vinylacetate copolymers, vinylpyrrolidon/dimethylamino ethylmethacrylate/vinyl caprolactam terpolymers as well as possibly derivatized cellulose ethers and silicones.

Suitable silicon compounds are for example dimethyl polysiloxane, methylphenyl polysiloxane, cyclic silicones as well as amino, fatty acid, alcohol, polyether, epoxy, fluorine, glykoside and/or alkyl modified silicon compounds, which at room temperatur can be in the liquid as well as in the resin state. Further suitable are simethicones, which are mixtures of dimethicones with an average chain length of 200 to 300 dimethyl siloxane units and hydrogenated silicates. A detailed survey of suitable volatile silicones can also be found in Todd et al., *Cosm. Toil.* 91 27 (1976).

Typical exemplary fats are glycerides, and as waxes natural waxes among others, can be used, such as e.g. candelilla wax, carnauba wax, Japan wax, espartogras wax, cork wax,-guaruma wax, rice seed oil wax, sugar-cane wax, ouricury wax, montan wax, beeswax, schellak wax, spermaceti, lanolin (wool wax), bürzel fat, ceresin, ozokerit (terrestrial wax), petrolatum, paraffin waxes, micro waxes; chemically modified waxes (hard waxes), such as e.g. montanester waxes, sasot waxes, hydrogenated yoyoba waxes as well as synthetic waxes, such as e.g. polyalkylene waxes and polyethylene glycol waxes.

As stabilizers metal salts of fatty acids, such as e.g. magnesium, aluminium and/or zinc stearate or ricinoleate can be used.

As biogenic active substances should be understood for example tocopherol, tocopherol acetate, tocopherol palmitate, ascorbic acid, desoxy ribonucleic acid, retinol, bisabolol, allantoin, phytantriol, panthenol, AHA acids, aminoacids, ceramides, pseudoceramides, essential oils, extracts of plants and vitamin complexes.

As deo active agents e.g. antiperspirants such as aluminium chlorohydrate come into question. This agent is in the form of colourless, hygroscopic crystals, which easily melt in air, and is obtained through evaporation of solutions of aluminium chloride in water. Aluminium chlorohydrate is used for manufacturing of perspiration inhibiting and deodorising preparations and has probably its effect through the partial closure of the perspiratory gland by means of precipitation of proteins and/or polysaccharides [see *J.Soc. Cosm.Chem.*24 281 (1973)]. Under the trade name Locron® of Hoechst AG, Frankfurt/FRG, an aluminium chlorohydrate is for example on the market, which corresponds to the formula $[Al_2(OH)_5Cl]\cdot 2.5\ H_2O$, and use of this is especially preferred (see *J.Pharm.Pharmacol.* 26, 531 (1975)]. In addition to the chlorohydrates also aluminium hydroxylactates as well as acid aluminium/zirconium salts can be used. As further deo active agents esterase inhibitors can be added. These are preferably trialkyl citrates such as trimethyl citrate, tripropyl citrate, triisopropyl citrate, tributyl citrate and especially triethyl citrate (Hydagen® CAT, Henkel KGaA, Düsseldorf/FRG). The substances inhibit the enzyme activity and thereby reduce the formation of odours. Probably the free acid is thereby set free through the cleavage of the citric acid ester, and this acid lowers the pH value of the skin so much that the enzymes thereby are inhibited. Further substances which can be used as estersase inhibitors are sterol sulphates or phosphates, such as for example lanosterol, cholesterol, campesterol, stigmasterol and sitosterol sulphate or phosphate, Dicarboxylic acids and their esters, such as for example glutaric acid, glutaric acid monoethylester, glutaric acid diethylester, adipic acid, adipic acid monoethylester, adipic acid diethylester, malonic acid and malonic acid diethylester, hydroxycarboxylic acids and their esters, such as for example citric acid, malic acid, tartaric acid or tartaric acid diethylester. Antibacterial active substances, which influence the germ flora and kill sweat destroyng bacterias or inhibit their growth, can also be contained in the pin preparations. Examples of this are chitosan, phenoxyethanol and chlorohexidin gluconate. Also 5chloro-2-(2,4-dichlorophen-oxy)phenol has shown to have an especially good effect, and this product is marketed unter the trade name lrgasan® by Ciba-Geigy, Basel/CH.

As anti dandruff agents climbazol, octopirox and zinc pyrethion can be used. Useable film formation agents are for example chitosan, microcrystalline chitosan, quatemary chitosan, polyvinylpyrrolidon, vinylpyrrolidon/vinylacetate copolymers, polymers of the acrylic acids, quaternary derivatives of cellulose, collagen, hyaluronic acid or its salts and similar compounds. As swelling agents for aqueous phases montmorillonite, clay mineral substances, pemulen, as well as alkylmodified Carbopol types (Goodrich) can be used. Further suitable polymers or swelling agents can be found in the survey of R.Lochhead in *Cosm.Toil*. 108, 95 (1993).

UV light protection factors are e.g organic substances (light protection filters) which by room temperature are in liquid or crystalline form, and which are capable of absorbing ultraviolet radiation and to set free the received energy in the form of radiation with long wavelength, e.g. in the form of heat. UVB filters can be soluble in oils or in water. As oil soluble substances the following are mentioned as examples:

3-Benzyliden camphor, respectively 3-benzylidene norcamphor and the derivatives thereof, e.g. 3-(4-methylbenzylidene)camphor as described in EP-B1 0693471;

4-aminobenzoic acid derivatives, preferably 4-(dimethylamino)benzoic acid 2-ethylhexylester, 4-(dimethylamino)benzoic acid 2-octylester and 4-(dimethylamino)benzoic acid amylester;

esters of cinnamonic acid, preferably 4-methoxy cinnamonic acid 2-ethylhexylester, 4-methoxy cinnamonic acid propylester, 4-methoxy cinnamonic acid isoamylester, 2-cyano-3,3-phenyl cinnamonic acid 2-ethythexylester (octocrylene);

esters of salicylic acid, preferably salicylic acid 2-ethylhexylester, salicylic acid 4-isopropyl benzylester, salicylic acid homomenthylester;

derivatives of benzophenone, preferably 2-hydroxy-4-methoxy benzophenone, 2-hydroxy-4-methoxy-4'-methyl benzophenone, 2,2'-dihydroxy-4-methoxy benzophenone;

esters of benzalmalonic acid, preferably 4-methoxy benzmalonic acid 2-ethylhexyl ester, triazine derivatives, such as e.g. 2,4,6-trianilino(p-carbo-2'-ethyl-1'-hexyloxy)-1,3,5-triazine and octyltriazone, as described in EP A1 0818450;

propane-1,3-diones, such as e.g.1-(4-tert.-butylphenyl)-3-(4'-methoxy-phenyl)-propane-1,3-dion;

ketotricyclo(5,2,1,0)-decane derivatives, as described in EP-B1 06945521. As water soluble substances the following can be mentioned:

2-Phenylbenzimidazol-5-sulphonic acid and the alkali, alkaline earth, ammonium, alkylammonium, alkanolammonium and glucammonium salts;

sulphonic acid derivatives of benzophenones, preferably 2-hydroxy-4-methoxybenzophenon-5-sulphonic acid and their salts;

sulphonic acid derivatives of 3-benzylidencamphen, such as e.g. 4-(2oxo-3-bomylidenmethyl)-benzene sulphonic acid and 2-methyl-5-(2-oxo-bomyliden) sulphonic acid and their salts.

As typical UV-A filters especially derivatives of benzoyl methane comes in question, such as e.g. 1-(4'-tert.-butylphenyl)-3-(4'-methoxyphenyl)propane-1,3-dion, 4-tert.butyl-4'-methoxydibenzoyl-methane (Parsol 1789), or 1-phenyl-3-(4'-isopropylphenyl-propane-1,3-dion. The UV-A and UV-B filters can of course also be used in mixtures. In addition to the mentioned soluble substances also insoluble light protection pigments can be used for this purpose, i.e. fine disperse metal oxides or salts. Examples of suitable metal oxides are especially zinc oxide and titanium dioxide and in addition other oxides of iron, zirconium, silicon, manganese, aluminium and cerium, as well as their mixtures. As salts silicates (talk), barium sulphate or zinc stearate can be used. The oxides and salts are used in the form of the pigments for skin caring and skin protecting emulsions and decorative cosmetics. The particles should have an average diameter of less than 100 nm, preferably between 5 and 50 nm and especially between 15 and 30 nm. They can have a spherical shape, but particles can also be used which have an ellipsoidal form or else have a shape which differs from the spherical shape. The pigments can also be present in a surface treated form, i.e. made hydrophiloc or htdrophobic. Typical examples are coated titanium dioxides, such as for example tTitanium dioxide T 805 (Degussa) or Eusolex® T2000 (Merck). As hydrophobic coating agents silicones and especially trialkoxy octyl silane or Simethicone can be used. In sun protecting agents preferably so-called micro or nano pigments are used. Preferably micronized zinc oxide is used. Further suitable UV light protection factors can be found in the survey by P.Finkel in *SÖFW-Joumal* 122, 543 (1996).

In addition to the two previously mentioned groups of primary light protection substances also secondary light protection substances of the antioxidant type find use, which interrupt the photochemichal reaction chain, which is initiated when UV radiation penetrates the skin. Typical examples of such are amino acids (e.g. glycin, histidin, tyrosin, tryptophan) and their derivatives, imidazoles (e.g. urocaninic acid) and their derivatives, peptides such as D,L-camosine, D-camosine, L-camosine and their derivatives (e.g. anserine), carotinoides, carotine (e.g. α-carotin, β-carotin, lycopin) and their derivatives, chlorogenic acid and its derivatives, liponic acid and its derivatives (e.g. dihydroliponic acid), aurothioglucose, propylthiouracil and other thiols (e.g. thiore-doxin, glutathion, cystein, cystin, cystamine and their glycosyl, n-acetyl, methyl, ethyl, propyl, amyl, butyl and lauryl, palmitoyl, oleyl, γ-linoleyl, cholesteryl and glyceryl esters) as well as their salts, dilauryl thiodipropionate, distearyl thiodipropionate, thiodipropionic acid and their derivatives (esters, ethers, peptides, lipides, nucleotides, nucleosides and salts) as well as sulfoximine compounds (e.g. buthionin sulfoximines, homocystein sulfoximines, butionin sulfones, penta-, hexa-, hepta-thionin sufoximine) in very small compatible doses (e.g. pmol to μmol/kg), further (metal) chelating agents (e.g. α-hydroxy fatty acids, palmitic acid, phytinic acid, lactoferrine), α-hydroxy acids (e.g. citric acid, lactic acid, malic acid), humin acid, gallic acid, gallic extracts, bilirubin, bifiverdin, EDTA, EGTA and their derivatives, unsaturated fatty acids and their derivatives (e.g. γ-linolenic acid, linolic acid, oleic acid), folic acid and their derivatives, ubichinon and ubichinol and their derivatives, vitamin C and derivatives (e.g. ascorbyl palmitate, Mg-ascorbyl phosphate, ascorbyl acetate), tocopheroles and derivatives (e.g. vitamin E acetate), vitamin A and derivatives (vitamin A patmitate) as well as koniferyl benzoate of benzoe resin, rutinic acid and their derivatives, α-glycosylrutin, ferula acid, furfuryliden glucitol, camosine, butylhydroxy toluene, butylhydroxy anisol, nordihydro guajak resin acid, nordihydro guajaret anisol, trihydroxy butyrophenon, uric acid and their derivatives, mannose and its derivatives, super oxide dismutase, zinc and its derivatives (e.g. ZnO, $ZnSO_4$), selen and its derivatives (e.g. selen-methionin), stilbenes and their derivatives (e.g. stilben oxide, trans-stilben oxide) and the derivatives suitable according to the invention (salts, esters, ethers, sugars, nucleotides, nucleosides, peptides and lipids) of these mentioned active substances.

For improvement of the flow properties further hydrotropes, such as for example ethanol, isopropyl alcohol, or polyols can be used. Polyols which in this case can be used preferably have 2 to 15 carbon atoms and at least two hydroxyl groups. The polyols can further contain additional functional groups, especially amino groups, or be modified with nitrogen. Typical examples are:

Glycerol;

alkylen glycols, such as for example ethylene glycol, diethylene glycol, propylene glycol, butylene glycol, hexylene glycol as well as polyethylen glycols with an average molecular weight from 100 to 1 000 Daltons;

oligoglycerol mixtures of technical quality with a self-condensation degree of 1.5 to 10, such as e.g. technical quality diglycerol mixtures with a diglycerol content of 40 to 50% by weight;

methyol compounds, such as especially trimethylol ethane, trimethylol propane, trimethylol butane, pentaerythrite and dipentaerythrite;

low alkyl glucosides, especially such with 1 to 8 carbons in the alkyl residue, such as for example methyl and butyl glucoside;

sugar alcohols with 5 to 12 carbon atoms, such as for example sorbitol or mannit;

sugars with 5 to 12 carbon atoms, such as for example glucose or saccharose;

aminosugars, such as for example glucamine;

dialcoholamines, such as diethanolamine or 2-amino-1,3-propanediol.

As preservatives are for example phenoxyethanol, formaldehyde solution, parabene, pentanediol or sorbic acid suited, and those mentioned in enclosure 6, parts A and B of the cosmetic regulation are further classes of substances. As insect repellents N,N-diethyl-m-toluamide, 1,2-pentanediol or insect repellent 3535 come into question, as self tanning agent dihydroxyaceton is suited.

As perfume oils mixtures of natural and synthetic scent substances should be mentioned. Natural scent substances are extracts of flowers (lilies, lavender, roses, jasmin, neroli, ylang-ylang), stems and blades (geranium, patchouli, petitgrain), fruits (anis, coriander, caraway, juniper), fruit shells (bergamot, lemon, orange), roots (macis, angelica, celery, kardamon, costus, iris, calmus), wood (stone pine, sandel, guajac, cedar, rosewood), herbs and grass (tarragon, lemongrass, sage, thyme), needles and twigs (spruce, fir, pine, traipsed), resins and balsams (galbanum, elemi, benzoe, myrrh, olibanum, opoponax). Raw materials from animals are also possible, such as for example zibet and castoreum. Typical synthetic odour compounds are products from types of esters, ethers, aldehydes, ketones, alcohols and hydrocarbons. Odour compounds from types of esters are e.g. benzyl acetate, phenoxyethyl isobutyrate, p-tert.-butylcyclohexyl acetate, linalyl acetate, dimethylbenzyl-carbinyl acetate, phenylethyl acetate, linalyl benzoate, benzyl formate, ethylmethylphenyl glycinate, allylcyclohexyl propionate, styrallyl propionate and benzyl salicylate. Benzylethyl ether belongs for example to the ethers, to the aldehydes e.g. the linear alkanales with 8 to 18 carbon atoms, citral, citronellal, citronellyl oxyacetaldehyde, cyclamen aldehyde, hydroxy citronellal, lilial and bourgeonal, to the ketones e.g. the ionones, $\alpha$-isomethyl ionon and methylcedryl ketone, to the alcohols anethol, citronellol, eugenol, isoeugenol, geraniol, linalool, phenylethyl alcohol and terpineol; to the hydrocarbons mainly the terpenes and balsams belong. However, mixtures of different odour substances are preferred, which together give a pleasant smell. Also etheral oils with low volatility, which often are used as aroma components, are suited as perfume oils, e.g. sage oil, chamomile oil, carnation oil, melissa oil, mint oil, cinnamon leaf oil, limeflower oil, juniper berry oil, vetiver oil, oliban oil, galbanum oil, labolanum oil and lavandin oil. Preferably used are bergamot oil, dihydromyrcenol, lilial, lyral, citronellol, phenylethyl alcohol, $\alpha$-hexylcinnamon aldehyde, geraniol, benzylaceton, cyclamen aldehyde, linalool, boisambrene forte, ambroxane, indol, hedione, sandelice, lemon oil, mandarin oil, orangenoil, allylamyl glycolate, cyclovertal, lavandine oil, muskateller sage oil, β-damascone, geranium oil bourbon, cyclohexyl salicylate, vertofix coeur, iso-E-super, fixolide NP, evernyl, iraidein gamma, phenylacetic acid, geranyl acetate, benzyl acetate, rose oxide, romillate, irotyl and floramate, alone or in mixtures.

As colouring agents such substances which are suited and approved for cosmetic purposes can be used, such as for example those mentioned in the publication "*Kosmetische Färbemittel*" (*cosmetic dyes*) *of the "Farbstoffkommission der Deutschen Forschungsgemeinschaft"*, published by Verlag Chemie, Weinheim, 1984, p. 81–106. These dyes are generally used in concentrations from 0.001 to 0.1% by weight, based on the whole mixture.

Typical examples of germ inhibiting substances are preservatives with specific effects against gram-positive bacteria, such as 2,4,4'-trichloro-2'-hydroxy diphenylether, chlorohexidin (1,6-di-(4-chlorophenyl-biguanido-hexan) or TCC (3,4,4'-trichlorocarbanilide). Many scent substances and etheral oils also have antimicrobial properties. Typical examples are the active agents eugenol, menthol and thymol in carnation, mint and thyme oil. An interesting natural deo substance is the terpene alcohol famesol (3,7,11-trimethyl-2,6,10-dodecatrien-1-ol), which is present in lime flower oil and has a smell of lilies of the valley. Also glycerol monolaurate have been used as bacteriostaticum. Normally the content of the further germ inhibiting agent is about 0.1 to 2% by weight—based on the solids content of the preparations.

The cumulative contents of the auxiliary and additional agents can be 1 to 50, preferably 5 to 40% by weight, based on the agents. The manufacture of the agents can take place by common cold or hot processes; preferably the work is carried out according to the phase inversion temperature method.

EXAMPLES

For the manufacture of the nanoscalar glucans (examples 1 to 3), carbon dioxide was first taken out of a reservoir with a constant pressure of 60 bar and cleaned over a column with active carbon and a pack of molecular sieves. After liquefaction the $CO_2$ was compressed to the required overcritical pressure by means of a diaphragma pump at a constant transported quantity of 3.5 l/h. Thereafter the solvent in a pre-heater was brought to the required temperature T1 and lead into an extraction column (steel, 400 ml), which had been loaded with the glucan. The resulting overcritical, i.e. fluid mixture, was through a long nozzle (lenght 830 µm, diameter 45 µm) at at temperature T2 sparayed into a plexiglas expansion chamber, which contained a 4 weight % aqueous solution of an emulsifier or a protecting colloid. The fluid medium evaporated and the dispersed nano particles, embedded in the protective colloid, were left. For manufacture of the nano particles according to example 4 a 1% by weight of an aqueous glucan solution by vigorous stirring at 40° C. and a redused pressure of 40 mbar, was dropwise added into a 4% by weight aqueous solution of coco glucosides. The evaproating solvent was condensed in a cold trap, and the dispersion with the nanoparticles was left back. The process conditions and the average particle size (photometrically determined according to the 3-WEM method) are stated in the following Table 1.

TABLE 1

| | | | | | | | |
|---|---|---|---|---|---|---|---|
| | | | | Nano Particles | | | |
| Ex. | Glucan | Solvent | p bar | T1 °C. | T2 °C. | Emulsifier/protection colloid | PGB nm |
| 1 | Betaglucan* | $CO_2$ | 200 | 80 | 175 | Polyvinyl alcohol | 50–125 |
| 2 | Betaglucan* | $CO_2$ | 180 | 70 | 160 | Polyethylen glycol (M = 400) | 70–130 |
| 3 | Betaglucan* | $CO_2$ | 200 | 85 | 175 | Coco glucosides | 50–150 |
| 4 | Betaglucan* | — | — | — | — | Cooo glucosides | 65–140 |

The following table contains a number of formulation examples with nano particles of glucan.

TABLE 2

Cosmetic preparations (water, preservatives ad 100% by weight)

| Composition (INCI) | 1 | 2 | 3 | 4 | 5 | 6 | 7 | 8 | 9 | 10 |
|---|---|---|---|---|---|---|---|---|---|---|
| Dehymuls ® PGPH<br>Polyglyceryl-2 dipolyhydroxystearate | 4.0 | 3.0 | — | 5.0 | — | — | — | — | — | — |
| Lameform ® TGI<br>Polyglyceryl-3 diisostearate | 2.0 | 1.0 | — | — | — | — | — | — | — | — |
| Emulgade ® PL 68/50<br>Cetearyl glucoside (and) cetearyl alcohol | — | — | — | — | 4.0 | — | — | — | 3.0 | — |
| Eumulgin ® B2<br>Ceteareth-20 | — | — | — | — | — | — | — | 2.0 | — | — |
| Tegocare ® PS<br>Polyglyceryl-3 methytglucose distearate | — | — | 3.0 | — | — | — | 4.0 | — | — | — |
| Eumulgin VL75<br>Polyglyceryl-2 dipolyhydroxystearate (and) lauryl glucoside (and) glycerol | — | — | — | — | — | 3.5 | — | — | 2.5 | — |
| Beeswax | 3.0 | 2.0 | 5.0 | 2.0 | — | — | — | — | — | — |
| Cutina ® GMS<br>Glyceryl stearate | — | — | — | — | — | 2.0 | 4.0 | — | — | 4.0 |
| Lanette ® O<br>Cetearyl alcohol | — | — | 2.0 | — | 2.0 | 4.0 | 2.0 | 4.0 | 4.0 | 1.0 |
| Antaron ® V 216<br>PVP/hexadecene copolymer | — | — | — | — | — | 3.0 | — | — | — | 2.0 |
| Mytritol ® 818<br>Coco glycerides | 5.0 | — | 10.0 | — | 8.0 | 6.0 | 6.0 | — | 5.0 | 5.0 |
| Finsolv ® TN<br>C12/15 Alkyl benzoate | — | 6.0 | — | 2.0 | — | — | 3.0 | — | — | 2.0 |
| Cetiol ® J 600<br>Oteyl erucate | 7.0 | 4.0 | 3.0 | 5.0 | 4.0 | 3.0 | 3.0 | — | 5.0 | 4.0 |
| Cetiol ® OE<br>Dicaprylyl ether | 3.0 | — | 6.0 | 8.0 | 6.0 | 5.0 | 4.0 | 3.0 | 4.0 | 6.0 |
| Mineral Oil | — | 4.0 | — | 4.0 | — | 2.0 | — | 1.0 | — | — |
| Cetiol ® PGL<br>Hexadecanol (and) hexyl laurate | — | 7.0 | 3.0 | 7.0 | 4.0 | — | — | — | 1.0 | — |
| Panthenol/Bisabolol | 1.2 | 1.2 | 1.2 | 1.2 | 1.2 | 1.2 | 1.2 | 1.2 | 1.2 | 1.2 |
| Nano-betaglucan according to example 1 | 1.0 | 1.0 | 1.0 | 1.0 | 1.0 | 1.0 | 1.0 | 1.0 | 1.0 | 1.0 |
| Copherol ® F 1300<br>Tocopherol/tocopheyl acetate | 0.5 | 1.0 | 1.0 | 2.0 | 1.0 | 1.0 | 1.0 | 2.0 | 0.5 | 2.0 |
| Neo Hellopan ® Hydro<br>Sodium phenylbenzimidazole sulphonate | 3.0 | — | — | 3.0 | — | — | 2.0 | — | 2.0 | — |
| Neo Hellopan ® 303<br>Octocrylene | — | 5.0 | — | — | — | 4.0 | 5.0 | — | — | 10.0 |
| Neo Heliopan ® BB<br>Benzophenone-3 | 1.5 | — | — | 2.0 | 1.5 | — | — | — | 2.0 | — |
| Neo Heliopan ® E 1000<br>Isoamyl p-metoxycinnamate | 5.0 | — | 4.0 | — | 2.0 | 2.0 | 4.0 | 10.0 | — | — |
| Neo Heliopan ® AV<br>Octyl metoxycinnamate | 4.0 | — | 4.0 | 3.0 | 2.0 | 3.0 | 4.0 | — | 10.0 | 2.0 |
| Uvinut ® T 150<br>Octyl triazone | 2.0 | 4.0 | 3.0 | 1.0 | 1.0 | 1.0 | 4.0 | 3.0 | 3.0 | 3.0 |
| Zinc oxide | — | 6.0 | 6.0 | — | 4.0 | — | — | — | — | 5.0 |
| Titanium dioxide | — | — | — | — | — | — | — | 5.0 | — | — |
| Glycerol (86% by weight) | 5.0 | 5.0 | 5.0 | 5.0 | 5.0 | 5.0 | 5.0 | 5.0 | 5.0 | 5.0 |

(1) W/O Sun protection creme,
(2–4) W/O Sun protection lotion,
(5, 8, 10) O/W Sun protection lotion
(6, 7, 9) O/W Sun protection creme

TABLE 2

Cosmetic preparations (water, preservatives ad 100% by weight) - (cont.)

| Composition (INCI) | 11 | 12 | 13 | 14 | 15 | 16 | 17 | 18 | 19 | 20 |
|---|---|---|---|---|---|---|---|---|---|---|
| Texapon ® NSO<br>Sodium laureth. sulphate | — | 30.0 | 30.0 | — | 25.0 | — | — | — | — | — |
| Plantacare ® 818<br>Coco glucosides | — | 10.0 | — | — | 20.0 | — | — | — | — | — |
| Plantacare ® PS 10<br>Sodium laureth. sulphate (and) coco glucosides | 22.0 | — | 5.0 | 22.0 | — | — | — | — | — | — |

TABLE 2-continued

Cosmetic preparations (water, preservatives ad 100% by weight) - (cont.)

| Composition (INCI) | 11 | 12 | 13 | 14 | 15 | 16 | 17 | 18 | 19 | 20 |
|---|---|---|---|---|---|---|---|---|---|---|
| Dehyton ® PK 45<br>Cocamidopropyl betaine | 15.0 | 10.0 | 15.0 | 15.0 | 20.0 | — | — | — | — | — |
| Emulgade ® SE<br>Glyceryl stearate (and) ceteareth. 12/20<br>(and) cetearyl alcohol (and) cetylpalmitate | — | — | — | — | — | 5.0 | 5.0 | 4.0 | — | — |
| Eumulgin ® B1<br>Ceteareth-12 | — | — | — | — | — | — | — | 1.0 | — | — |
| Lameform ® TGI<br>Polyglyceryl-3 isostearate | — | — | — | — | — | — | — | — | 4.0 | — |
| Dehymuls ® PGPH<br>Polyglyceryl-2 dipolyhydroxystearate | — | — | — | — | — | — | — | — | — | 4.0 |
| Monomuls ® 90-O 18<br>Glyceryl oleate | — | — | — | — | — | — | — | — | 2.0 | — |
| Cetiol ® HE<br>PEG-7 Glyceryl cocoate | 2.0 | — | — | 2.0 | 5.0 | — | — | — | — | 2.0 |
| Cetiol ® OE<br>Dicaprylyl ether | — | — | — | — | — | — | — | — | 5.0 | 6.0 |
| Cetiol ® PGL<br>Hexyldecanol (and) hexyldecyl laurate | — | — | — | — | — | — | — | 3.0 | 10.0 | 9.0 |
| Cetiol ® SN<br>Cetearyl isononanoate | — | — | — | — | — | 3.0 | 3.0 | — | — | — |
| Cetiol ® V<br>Decyl oleate | — | — | — | — | — | 3.0 | 3.0 | — | — | — |
| Myritol ® 318<br>Coco caprylate caprate | — | — | — | — | — | — | — | 3.0 | 5.0 | 5.0 |
| Beeswax | — | — | — | — | — | — | — | — | 7.0 | 5.0 |
| Nutrilan ® Elastin E20<br>Hydrolyzed elastin | — | — | — | — | — | 2.0 | — | — | — | — |
| Nutrilan ® I-50<br>Hydrolyzed collagen | — | — | — | — | 2.0 | — | 2.0 | — | — | — |
| Gluadin ® AGP<br>Hydrolyzed wheat glutene | 0.5 | 0.5 | 0.5 | — | — | — | — | 0.5 | — | — |
| Gluadin ® WK<br>Sodium cocoyl hydrolyzed wheat protein | 2.0 | 2.0 | 2.0 | 2.0 | 5.0 | — | — | — | 0.5 | 0.5 |
| Eupertan ® PK 3000 AM<br>Glycol distearate (and) laureth-4 (and) cocamidopropyl betaine | 5.0 | — | — | 5.0 | — | — | — | — | — | — |
| Arylpon ® F<br>Laureth.-2 | — | — | — | — | — | — | — | — | — | — |
| Highcareen ® GS<br>Betaglucan | 1.0 | 1.0 | 1.0 | 1.0 | 1.0 | 1.0 | 1.0 | 1.0 | 1.0 | 1.0 |
| Magnesium sulphate heptahydrate | — | — | — | — | — | — | — | — | 1.0 | 1.0 |
| Glycer I (86% by weight) | — | — | — | — | — | 3.0 | 3.0 | 5.0 | 5.0 | 3.0 |

(11–15) Foam bath,
(16) Soft creme,
(17, 18) Moisture emulsion,
(19, 20) Night creme

We claim:

1. A method for improved glucan resorption in skin or hair comprising applying to the skin or hair a cosmetic composition comprising nanoparticulate water-soluble β-(1,3)-glucans, which have intact β-(1,3) side chains and are free from repetitive β-(1,6) linkages and have particle diameters of about 10 to 300 nm.

2. The method according to claim 1, comprising glucans based on yeast of the family *Saccharomyces*.

3. The method according to claim 1, wherein the nanoparticulate glucans are embedded in a protective colloid.

4. The method according to claim 3, wherein the protective colloid is selected from the group consisting of polyvinyl alcohol and polyethylene glycol.

5. The method according to claim 1, wherein the glucan is present in the amount of about 0.1% to about 5% by weight relative to the cosmetic composition.

6. The method according to claim 1, wherein the nanoparticulate water-soluble β-(1,3)-glucans have improved resorption in skin and hair.

7. The method according to claim 1, wherein cosmetic composition is a sun radiation protective agent.

8. A method of preparing glucans for use in a cosmetic composition which has improved glucan resorption comprising the steps of:

(a) preparing water-soluble β-(1,3)-glucans, which have intact β-(1,3) side chains and are free from repetitive β-(1,6) linkages and have particle diameters of about 10 to 300 nm, by the process comprising contacting glucan β-(1,3) and β-(1,6) linkages with β-(1,6) glucanases to loosen substantially all β-(1,6) linkages and reducing the size of the resulting glucans into nanoparticulate form, and (b) embedding the nanoparticulate glucans in a protective colloid.

9. The method according to claim 8, wherein the reduction of the size of the resulting glucans into nanoparticulate form comprises the steps of:
 a) dissolving the water-soluble β-(1,3) glucans under supercritical conditions
 b) relaxing fluid pressure through a nozzle in a vacuum, gas or liquid, and
 c) evaporating the solvent.

10. The method according to claim 9, wherein the conditions for dissolving the water-soluble solvent are close to critical condition.

11. The method according to claim 8, wherein the protective colloid is selected from the group consisting of polyvinyl alcohol and polyethylene alcohol.

12. The method according to claim 9, wherein the glucan is present in the amount of about 0.1% to 5% by weight relative to the cosmetic composition.

13. A cosmetic composition comprising nanoparticulate water-soluble β-(1,3)-glucans, which have intact β-(1,3) side chains and are free from repetitive β-(1,6) linkages and have particle diameters ranging in size from about 10 to 300 nm. embedded in a protective colloid.

14. The cosmetic composition of claim 13, wherein the glucan is present in the amount of about 0.1% to about 5% by weight.

* * * * *